United States Patent [19]

Harada et al.

[11] Patent Number: 5,110,952
[45] Date of Patent: May 5, 1992

[54] METHOD OF PRODUCING 3-DIBUTYLAMINO 6-METHYL-7-ANILINOFLUORAN

[75] Inventors: Hiroaki Harada; Yasuhisa Iwasaki, both of Yao, Japan

[73] Assignee: Yamamoto Chemicals, Inc., Osaka, Japan

[21] Appl. No.: 631,677

[22] Filed: Dec. 20, 1990

[30] Foreign Application Priority Data

Dec. 25, 1989 [JP] Japan .................................. 1-337994

[51] Int. Cl.$^5$ .......................................... C07D 311/82
[52] U.S. Cl. ..................................................... 549/226
[58] Field of Search ......................................... 549/226

[56] References Cited

U.S. PATENT DOCUMENTS

| | | | |
|---|---|---|---|
| 4,017,710 | 5/1991 | Igaki et al. | 549/226 |
| 4,341,403 | 7/1982 | Igarashi et al. | 549/226 |
| 4,536,220 | 8/1985 | Kondo et al. | 549/226 |
| 4,749,796 | 6/1988 | Sensui et al. | 549/226 |
| 4,806,657 | 2/1989 | Zink | 549/226 |
| 4,837,210 | 6/1989 | Dwyes-Hallquist et al. | 569/226 |

FOREIGN PATENT DOCUMENTS

| | | | |
|---|---|---|---|
| 9120654 | 7/1984 | Japan | 549/226 |
| 9157153 | 9/1984 | Japan | 549/226 |
| 38469 | 2/1985 | Japan | 549/226 |
| 47068 | 3/1985 | Japan | 549/226 |

*Primary Examiner*—Cecilia Shen
*Attorney, Agent, or Firm*—Wenderoth, Lind & Ponack

[57] ABSTRACT

A method of producing a high melting point 3-dibutyl amino-6-methyl-7-anilinofluoran characterized by peaks at diffraction angle (2 $\theta$) of 6.9°, 11.0°, 18.5° and 18.9° in X-ray diffractiometry using Cu-K $\alpha$ ray and having a melting point in the range of 179°–186° C., which comprises: condensing 2-(4-dibutylamino-2-hydroxy-benzoyl) benzoic acid with 4-methoxy-2-methyldiphenylamine in the presence of concentrated sulfuric acid to provide a phthalide at a temperature in the range of 0°–50° C., neutralizing the phthalide, and then subjecting the phthalide to ring closure reaction using an alkali in an amount of 0.5–15 mols per mol of the compound used in smaller amounts of 2-(4-dibutylamino-2-hydroxy-benzoyl) benzoic acid and 4-methoxy-2-methyldiphenylamine at a temperature of not less than 50° C. in the presence or absence of an organic solvent.

5 Claims, 1 Drawing Sheet

METHOD OF PRODUCING 3-DIBUTYLAMINO 6-METHYL-7-ANILINOFLUORAN

BACKGROUND OF THE INVENTION

This invention relates to a method of producing 3-dibutylamino-6-methyl-7-anilinofluoran having a melting point in the range of 179°-186° C.

The contact of a colorless or only slightly colored proton donating leuco compound or a color former with an electron accepting acidic compound or a color developer under physical force or heat produces a colored substance. This is a well known phenomenon and is widely used in pressure or heat sensitive recording.

3-Dibutylamino-6-methyl-7-anilinofluoran is one of the color formers in wide use. It is known that the fluoran compound has three crystal modifications: high melting point compound which is characterized by peaks at diffraction angle ($2\theta$) of 6.9°, 11.0°, 18.5° and 18.9° in X-ray diffractiometry using Cu-K $\alpha$ ray and having a melting point in the range of 179°-186° C.; a low melting point compound which has a melting point in the range of 146°-155° C.; and an amorphous type compound which has a melting point of 85°-95° C. Among these three crystal modifications, the high melting point compound is more excellent than any other in, in particular, color darkness and resistance to background coloration when used as a color former in pressure or heat sensitive recording material.

There is described in Japanese Patent Laid-open No. 60-202155 that a known conventional method provides a low melting type 3-dibutylamino-6-methyl-7-anilinofluoran. The conventional method is as follows. 2-(4-Dibutylamino-2-hydroxybenzoyl)benzoic acid and 4-methoxy-2-methyldiphenylamine are dissolved in concentrated sulfuric acid, and the reaction is carried out at 0°-5° C. for 20 hours. After the reaction, the reaction mixture is poured into ice water, whereupon precipitates are formed. The precipitates are collected by filtration and washed with water to provide a cake of 3-(4-dibutylamino-2-hydroxyphenyl)-3-(5-anilino-2-methoxyphenyl)phthalide. The cake is added to a mixture of toluene and water, and then the mixture is neutralized with a 28% by weight aqueous solution of sodium hydroxide. A further amount of sodium hydroxide is added and then the mixture is stirred at a refluxing temperature for three hours. After the reaction, the mixture is left standing, and a toluene layer is separated and concentrated at 70° C. until a syrup is obtained. Methanol is added to the syrup so that 3-dibutylamino-6-methyl-7-anilinofluoran crystalizes out. According to the reference, the obtained compound has a melting point of 148°-152° C.

Thus, the above prior art reference proposes a method of producing the high melting point compound by first preparing the low melting point compound in the manner as described above, and then heating the compound at temperatures of not less than 70° C. together with chlorobenzenes over a period of not less than 30 minutes.

A further method is also proposed in the reference, in which the phthalide is collected by filtration, added to a mixture of chlorobenzene and water, neutralized with an aqueous solution of sodium hydroxide, and then sodium hydroxide is added to the mixture, followed by stirring at 80°-85° C. Then a chlorobenzene layer is separated and heated at 110°-120° C. to convert the low melting point compound to the high melting compound.

The above methods need the treatment of the low melting compound with chlorobenzenes to convert it to the high melting compound. Thus, the methods are disadvantageous from the standpoint of process economy, and also the yield of the high melting point compound is low as the method needs steps of operations.

SUMMARY OF THE INVENTION

It is an object of the invention to obviate the above mentioned problems involved in the prior art, and to provide a method of producing a high melting point 3-dibutylamino-6-methyl-7-anilinofluoran in an inexpensive manner without the specific treatment for conversion of the low melting to the high melting point compound.

The invention provides a method of producing a high melting point 3-dibutylamino-6-methyl-7-anilinofluoran characterized by peaks at diffraction angle ($2\theta$) of 6.9°, 11.0°, 18.5° and 18.9° in X-ray diffractiometry using Cu-K $\alpha$ ray and having a melting point in the range of 179°-186° C., which comprises: condensing 2-(4-dibutylamino-2-hydroxybenzoyl)benzoic acid with 4-methoxy-2-methyldiphenylamine in the presence of concentrated sulfuric acid to provide a phthalide at a temperature in the range of 0°-50° C., neutralizing the phthalide, and then subjecting the phthalide to ring closure reaction using an alkali in an amount of 0.5-15 mols per mol of the compound used in smaller amounts of 2-(4-dibutylamino-2-hydroxybenzoyl)benzoic acid and 4-methoxy-2-methyldiphenylamine in the presence or absence of an organic solvent.

DESCRIPTION OF THE PREFERRED EMBODIMENTS

Figure 1:
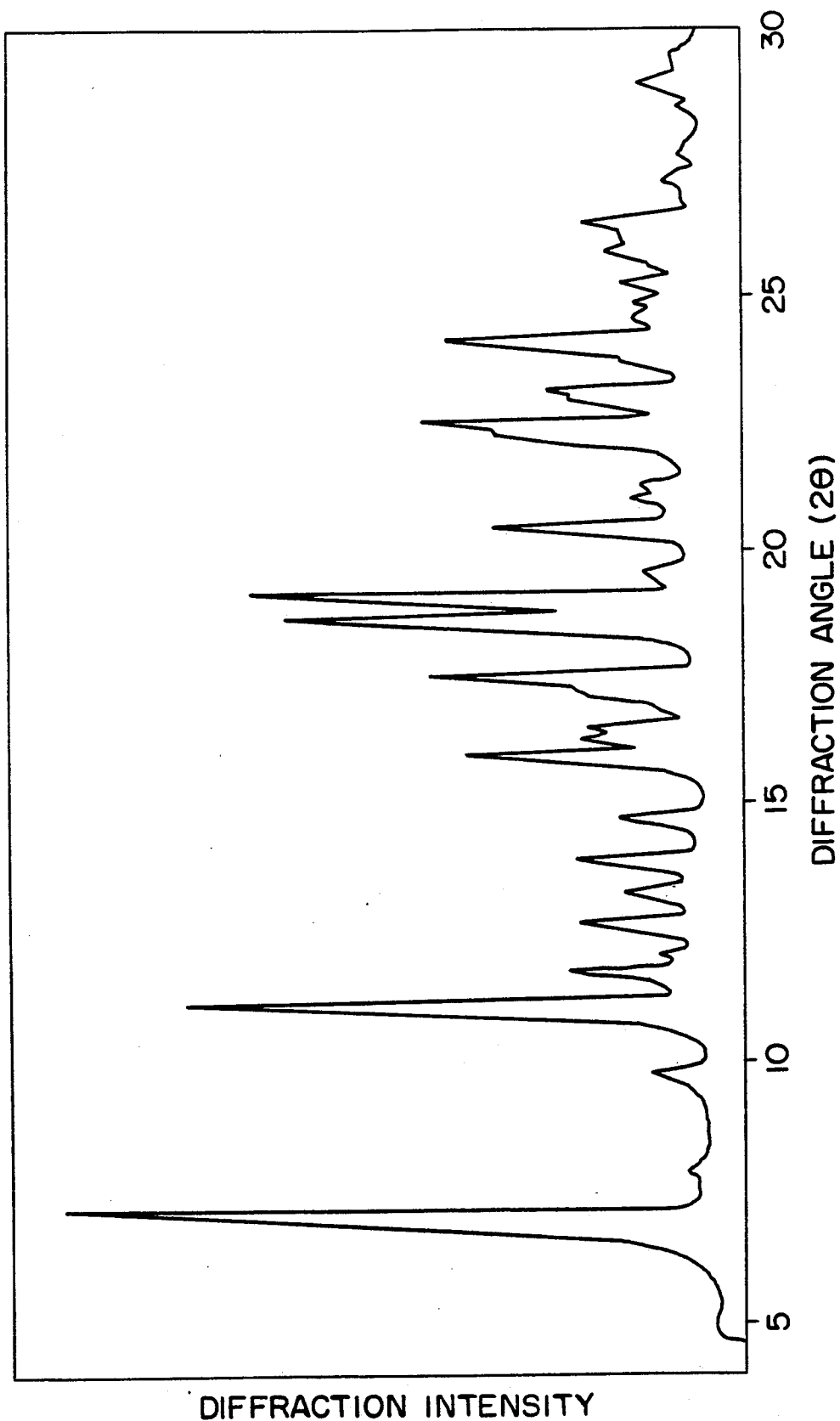

According to the method of the invention, 2-(4-dibutylamino-2-hydroxybenzoyl)benzoic acid is first reacted with 4-methoxy-2-methyldiphenylamine in the presence of concentrated sulfuric acid to provide a phthalide. In this condensation reaction, the amine is used in an amount of 0.8-1.2 mols per mol of the starting benzoic acid derivative, whereas concentrated sulfuric acid is used in an amount of 1.5-8 parts by weight per part by weight of the starting benzoic acid derivative. The reaction is carried out at temperatures usually of 0°-50° C. for 5-50 hours.

After the reaction, the resultant reaction mixture is added to water whereupon the phthalide crystallizes out, and the phthalide is collected by filtration and washed with water, followed by neutralization of the phthalide with an aqueous alkali solution. Then an allaki is further added to the phthalide and heated at temperatures of not less than 50° C. to subject the phthalide to ring closure reaction, thereby to provide the high melting point 3-dibutylamino-6-methyl-7-anilinofluoran.

In the above ring closure reaction, there may be preferably used as the alkali, for example, sodium hydroxide, potassium hydroxide, sodium carbonate or potassium carbonate. These alkalis are used as aqueous solutions usually of a concentration of 3-50% by weight, preferably of 20-40% by weight. Further, the alkali is used in an amount of 0.5-15 mols, preferably in an amount of 2-10 mols, per mol of the compound used in smaller amounts of 2-(4-dibutylamino-2-hydroxybenzoyl)benzoic acid and 4-methoxy-2-methyldiphenylamine. Since the higher the temperature of the ring closure temperature, the more promptly and efficiently the reaction proceeds, the reaction is preferably carried out at reflux temperatures.

In accordance with the invention, the ring closure reaction is preferably carried out in the presence of an organic solvent. The solvent used is not specifically limited provided that it is insoluble or only slightly soluble in water. Thus, the solvent may be exemplified by aromatic hydrocarbons such as benzene, toluene, xylene or trimethylbenzenes, halogenated aromatic hydrocarbons such as chlorobenzene, dichlorobenzenes, trichlorobenzenes or bromonaphthalenes, halogenated aliphatic hydrocarbons such as dichloroethane or tetrachloroethane, aliphatic hydrocarbons such as hexane, heptane, octane or n-decane, and alicyclic hydrocarbons such as cyclohexane or methylcyclohexane. In addition to the above, there may also be used alcohols such as amyl alcohol or octyl alcohol, ethers such as isopropyl ether, or ketones such as cyclohexanone. The solvent may be used singly or as a mixtures.

After the reaction, the reaction mixture is filtered, washed with water to remove the alkali used or subjected to funnel separation to remove an alkali layer, washed with warm water, and then concentrated or dried, to provide the high melting point 3-dibutylamino-6-methyl-7-anilinofluoran as colorless or only slightly colored crystals. When necessary, the product may be further purified by recrystallization.

The invention will be described more specifically with reference to examples, but the invention is not limited thereto.

EXAMPLE 1

An amount of 36.9 g of 2-(4-dibutylamino-2-hydroxybenzoyl)benzoic acid and 21.3 g of 4-methoxy-2-methyldiphenylamine were dissolved in 100 ml of concentrated sulfuric acid at 30° C., and the mixture was stirred at the temperature for 20 hours. After the reaction, the resultant reaction mixture was added to one liter of ice water, and the resultant precipitates were collected by filtration and fully washed with water.

The solid were dispersed in 500 ml of water, and an aqueous solution of sodium hydroxide was added thereto to neutralize the sulfuric acid. A further amount of 15 g of sodium hydroxide was added to the mixture to make the dispersion alkaline, and then the mixture was stirred under heating, whereupon the solid was dispersed as very fine particles in the mixture. The solid was collected by filtration, washed with water and dried.

The solid was recrystallized from toluene, to provide 40.5 g (76.1% yield) of 3-dibutylamino-6-methyl-7-anilinofluoran as colorless solid having a melting point of 181.5°-183.5° C. FIG. 1 is an X-ray diffraction pattern (Cu-K α) of the crystals. The compound was found to have characteristic peaks at diffraction angle (2θ) of 6.9°, 11.0°, 18.5° and 18.9°.

An solution of the compound in toluene was colorless, but turned to reddish black when being put into contact with silica gel.

EXAMPLE 2

An amount of 36.9 g of 2-(4-dibutylamino-2-hydroxybenzoyl)benzoic acid and 21.3 g of 4-methoxy-2-methyldiphenylamine were dissolved in 100 ml of concentrated sulfuric acid at 30° C., and the mixture was stirred at the temperature for 20 hours. After the reaction, the resultant reaction mixture was added to one liter of ice water, and the resultant precipitates were collected by filtration and fully washed with water.

The solid were dispersed in 500 ml of water, and an aqueous solution of sodium hydroxide was added thereto to neutralize the sulfuric acid. A further amount of 15 g of sodium hydroxide and 200 ml of toluene were added to the mixture, and the mixture was stirred under refluxing. After cooling, the aqueous layer of the mixture containing sodium hydroxide was separated, the organic layer was washed with warm water, and then the toluene was removed by distillation. An amount of 150 ml of methanol was added to the concentrate to disperse the solid therein, the solid was collected by filtration, washed with methanol, and dried, to provide 42.7 g (80.0% yield) of 3-dibutylamino-6-methyl-7-anilinofluoran as colorless solid having a melting point of 181.2°-184.8° C. The X-ray diffraction pattern of the solid was the same as FIG. 1.

EXAMPLE 3

An organic solvent as shown in the table 1 was used in place of toluene and otherwise in the same manner as in the Example 2, the reaction was carried out. The resultant products were all high melting point 3-dibutylamino-6-methyl-7-anilinofluoran based on their melting points and X-ray diffraction study.

TABLE 1

| Example No. | Solvent | Melting Point (°C.) |
| --- | --- | --- |
| 3 | Benzene | 180.5–185.5 |
| 4 | Xylene | 180.5–185.0 |
| 5 | Trimethylbenzene | 180.0–186.0 |
| 6 | Chlorobenzene | 181.0–185.5 |
| 7 | Dichlorobenzene | 179.5–184.5 |
| 8 | Trichlorobenzene | 181.0–186.0 |
| 9 | Amyl alcohol | 179.5–185.0 |
| 10 | Octyl alcohol | 181.5–185.5 |
| 11 | Dichloroethane | 180.5–184.0 |
| 12 | Tetrachlorobenzene | 179.5–185.0 |
| 13 | Octane | 179.0–183.5 |
| 14 | n-Decane | 179.0–184.5 |
| 15 | Bromonaphthalene | 181.0–185.0 |

What is claimed is:

1. A method of producing a high melting point 3-dibutylamino-6-methyl-7-anilinofluoran characterized by peaks at diffraction angle (2θ) of 6.9°, 11.0°, 18.5° and 18.9° in X-ray diffractiometry using Cu-K α ray and having a melting point in the range of 179°–186° C., which comprises: condensing (A) 2-(4-dibutylamino-2-hydroxy-benzoyl)benzoic acid with (B) 4-methoxy-2-methyldiphenylamine in an amount of 0.8 to 1.2 mols (A) per mol (B), in the presence of concentrated sulfuric acid to provide a phthalide at a temperature in the range of 0°–50° C., neutralizing the phthalide, and then subjecting the phthalide to ring closure reaction using an alkali in an amount of 0.5–15 mols per mol of (A) or (B), the selection of (A) or (B) being determined by the one used in the smallest amount at a temperature of not less than 50° C. up to the reflux temperature in the presence or absence of a water immiscible organic solvent.

2. The method as claimed in claim 1 wherein the ring closure reaction is carried out in the presence of an organic solvent which has a boiling point of not less than 60° C.

3. The method as claimed in claim 2 wherein the organic solvent is an aromatic hydrocarbon, a halogenated aromatic hydrocarbon, a halogenated aliphatic hydrocarbon, an aliphatic hydrocarbon or an alicyclic hydrocarbon.

4. The method as claimed in claim 2 wherein the organic solvent is amyl alcohol or octyl alcohol.

5. The method as claimed in claim 1 wherein the alkali is used in an amount of 2–10 mols per mol of (A) or (B), the selection of (A) or (B) being determined by the one used in the smallest amount.

* * * * *

REEXAMINATION CERTIFICATE (3772nd)

United States Patent [19]

Harada et al.

[11] B1 5,110,952
[45] Certificate Issued Jun. 1, 1999

[54] METHOD OF PRODUCING 3-DIBUTYLAMINO 6-METHYL-7-ANILINOFLUORAN

[75] Inventors: Hiroaki Harada; Yasuhisa Iwasaki, both of Yao, Japan

[73] Assignee: Yamamoto Chemicals, Inc., Osaka, Japan

Reexamination Request:
No. 90/005,108, Sep. 16, 1998

Reexamination Certificate for:
Patent No.: 5,110,952
Issued: May 5, 1992
Appl. No.: 07/631,677
Filed: Dec. 20, 1990

[30] Foreign Application Priority Data

Dec. 25, 1989 [JP] Japan ................. 1-337994

[51] Int. Cl.$^6$ ................. C07D 311/82
[52] U.S. Cl. ................. 549/226
[58] Field of Search ................. 549/226

[56] References Cited

U.S. PATENT DOCUMENTS

Re. 33,815  2/1992  Yamaguchi et al. ................. 503/214

FOREIGN PATENT DOCUMENTS 60-202155  10/1985  Japan.

Primary Examiner—Bernard Dentz

[57] ABSTRACT

A method of producing a high melting point 3-dibutyl amino-6-methyl-7-anilinofluoran characterized by peaks of diffraction angle (2 θ) of 6.9°, 11.0°, 18.5° and 18.9° in X-ray diffractiometry using Cu-K α ray and having a melting point in the range of 179°–186° C., which comprises: condensing 2-(4-dibutylamino-2-hydroxy-benzoyl) benzoic acid with 4-methoxy-2-methyldiphenylamine in the presence of concentrated sulfuric acid to provide a phthalide at a temperature in the range of 0°–50° C., neutralizing the phthalide, and then subjecting the phthalide to ring closure reaction using an alkali in an amount of 0.5–15 mols per mol of the compound used in smaller amounts of 2-(4-dibutylamino-2-hydroxy-benzoyl) benzoic acid and 4-methoxy-2-methyldiphenylamine at a temperature of not less than 50° C. in the presence or absence of an organic solvent.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-5 is confirmed.

* * * * *